United States Patent [19]
Alferness et al.

[11] Patent Number: 5,330,506
[45] Date of Patent: Jul. 19, 1994

[54] REDUCED CURRENT CARDIAC PACING APPARATUS

[75] Inventors: Clifton A. Alferness, Redmond, Wash.; Raymond E. Ideker, Durham, N.C.

[73] Assignee: Physio-Control Corporation, Redmond, Wash.

[21] Appl. No.: 125,080

[22] Filed: Sep. 21, 1993

Related U.S. Application Data

[63] Continuation of Ser. No. 713,169, Jun. 11, 1991, abandoned.

[51] Int. Cl.[5] .............................................. A61N 1/36
[52] U.S. Cl. ......................................... 607/10; 607/66; 607/70
[58] Field of Search .................. 607/5, 9–10, 607/14, 15, 34, 66, 67, 68, 70, 72

[56] References Cited

U.S. PATENT DOCUMENTS

| | | | |
|---|---|---|---|
| 3,626,926 | 12/1971 | Kuzin et al. | 128/420 A |
| 3,774,620 | 11/1973 | Hansjürgens | 128/420 A |
| 3,895,639 | 6/1975 | Rodler | 128/422 |
| 3,958,577 | 5/1976 | Rodler | 128/420 A |
| 4,148,321 | 4/1979 | Wyss et al. | 128/420 |
| 4,280,504 | 7/1981 | Rodler | 128/420 A |
| 4,401,121 | 8/1983 | Rodler | 128/420 A |
| 4,467,807 | 8/1984 | Bornzin | 128/419 PG |
| 4,708,145 | 11/1987 | Tacker, Jr. et al. | 128/419 D |

FOREIGN PATENT DOCUMENTS

| | | | |
|---|---|---|---|
| 2257312 | 8/1975 | France | 128/419 D |
| WO88/03822 | 6/1988 | PCT Int'l Appl. | |
| 1337824 | 11/1973 | United Kingdom. | |
| 2110935 | 6/1983 | United Kingdom. | |

OTHER PUBLICATIONS

Bourland et al., "Medical Instrumentation" vol. 20, No. 3, May–Jun. 1986 pp. 138–142.
European Search Report, dated Dec. 8, 1992.

*Primary Examiner*—William E. Kamm
*Assistant Examiner*—Jeffrey R. Jastrzab
*Attorney, Agent, or Firm*—Christensen, Connor, Johnson & Kindness

[57] ABSTRACT

A cardiac pacing apparatus and method. A cardiac pacing apparatus (24) provides a cardiac pacing signal to a plurality of electrode pairs (20, 22), each comprising a positive electrode (20a, 22a) and a negative electrode (20b, 22b). A plurality of isolated current sources (30, 32) supply the electrode pairs with separate electric pacing currents, each small enough in magnitude so as to avoid patient discomfort or burning. The plurality of pacing currents delivered to the electrode pairs add to produce a total cardiac pacing current of sufficient magnitude to cause contraction of a heart muscle through which the pacing currents flow.

21 Claims, 3 Drawing Sheets

REDUCED CURRENT CARDIAC PACING APPARATUS

This application is a continuation application based on prior copending application Ser. No. 07/713,169, filed on Jun. 11, 1991 now abandoned.

FIELD OF THE INVENTION

The present invention relates to a cardiac pacing apparatus, and in particular, to an apparatus and method for providing low-current cardiac pacing signals.

BACKGROUND OF THE INVENTION

There are two major pumping chambers in the heart, the left and right ventricles. Contracting simultaneously, these chambers pump blood into the aorta and the pulmonary artery. Blood enters the ventricles from the left and right atria and is forced into the ventricles by an atrial contraction, which precedes a major ventricular contraction by an interval of about 100 milliseconds. This interval is known as the atrial ventricular (AV) delay. In a healthy heart, the atrial and ventricular contractions begin with a wave of electrical excitation that originates in the right atrium and spreads to the left atrium. This excitation of the cardiac muscle then spreads to the AV node, which delays its passage to the ventricles. Generally, such atrial excitations begin every 400–1,000 milliseconds at a metabolically-determined frequency known as the sinus rate. Sometimes however, in a diseased or damaged heart, such electrical excitation signals are either not properly produced or do not reach the heart muscle. In either case, the heart will not pump blood properly.

Traditionally, the cure for such a heart condition, when permanent, has been to implant an internal cardiac pacemaker that electrically supplies the necessary excitation pacing signals through a set of electrodes connected directly to the heart. Such electrodes may include a single electrode or pairs of electrodes that deliver the pacing currents to various areas of the heart muscle. Until a permanent cardiac pacemaker can be surgically implanted, a patient suffering from such a heart condition may need to have such pacing signals applied externally using a cardiac pacemaker in order to stay alive. Such pacing signals may be applied continuously if the heart is completely malfunctioning, or intermittently if it is only occasionally malfunctioning.

External cardiac pacers are also used to restore a temporarily malfunctioning heart to normal operation, as can occur, for example, after electrical shock. Generally, such an external pacer includes a set of electrodes that are placed in electrical contact with the patient's chest. The pacer delivers an electric current large enough to stimulate the heart muscle and contract it, thereby pumping blood.

The problem with such external cardiac pacers is that the pacing currents delivered to the external electrodes are sometimes sufficiently great to cause burning or severe discomfort and pain to the patient at the site where the electrodes are placed. To overcome this problem, attempts have been made to reduce the current density at the site where the individual pacing electrodes are placed during cardiac pacing. One such attempt involved the use of pacing electrodes having a large surface area. However, such electrodes did not prove successful in reducing patient discomfort. Therefore, it remains desirable to have a pacing system that will provide a pacing current to the heart muscle with a reduced current density to avoid causing severe burns or discomfort to the patient.

SUMMARY OF THE INVENTION

In accordance with the present invention, disclosed is an external cardiac pacing apparatus for providing a total cardiac pacing signal to a patient's heart muscle. An electrical current source is coupled to a plurality of electrode pairs, which are attachable to the patient. The electrical current source provides each of the electrode pairs with an individual electrical current. The individual electrical currents cooperatively form the total cardiac pacing signal. The magnitude of the electric pacing current supplied by the current source to each of the electrode pairs is less than the total pacing current required to cause contraction of a heart muscle in order to reduce patient discomfort.

DETAILED DESCRIPTION OF THE PREFERRED EMBODIMENTS

Figure 1:
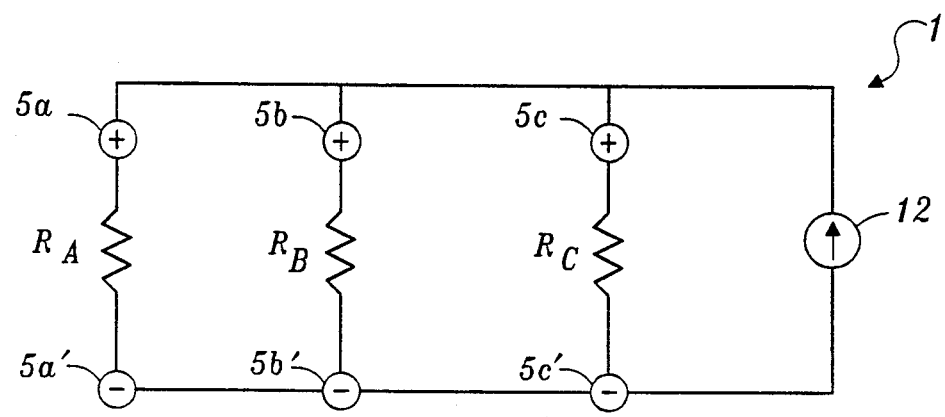
FIG. 1 is an electrical schematic diagram of a reduced current pacing apparatus according to a first embodiment of the present invention.

FIG. 1 is a first embodiment of a reduced current cardiac pacing apparatus according the present invention, shown generally at reference numeral 1. A set of pacing electrodes 5 comprises a plurality of positive electrodes 5a, 5b, and 5c and a plurality of negative electrodes 5a', 5b' and 5c'. When the set of pacing electrodes 5 is placed on a patient, there exists between electrodes 5a and 5a' an impedance Ra. An impedance Rb exists between electrodes 5b and 5b', and an impedance Rc exists between electrodes 5c and 5c'. A common pacing current source 12 supplies a pacing current to each of the parallely-connected electrode pairs 5a and 5a', and 5b and 5b', and 5c and 5c'. The pacing current applied to the plurality of electrodes will divide among the electrode pairs according the magnitude of the impedances Ra, Rb, and Rc. If the magnitude of these impedances is relatively equal, then the pacing current will divide equally among the electrode pairs. Patient burning and discomfort can be reduced if the current carried by each pair of electrodes is roughly one-third of the total current needed to contact a patient's heart muscle.

If one of the impedances Ra, Rb, or Rc is substantially smaller than the other two, most of the current from pacing current source 12 will flow along the path of the lowest impedance. Should this current be large enough, patient discomfort or burning may occur. Because the relative impedances Ra, Rb, and Rc cannot be controlled, there may be no practical way to arrange a plurality of electrodes in parallel to ensure that the impedance between each pair of electrodes will be the same and that an equal amount of current will flow through each electrode pair. However, such a parallel arrangement of electrodes is preferable to a single electrode pair because human physiology tends to keep the impedances between the electrodes roughly equal so that the total pacing currents will divide equally through the individual electrode pairs.

Figure 2:
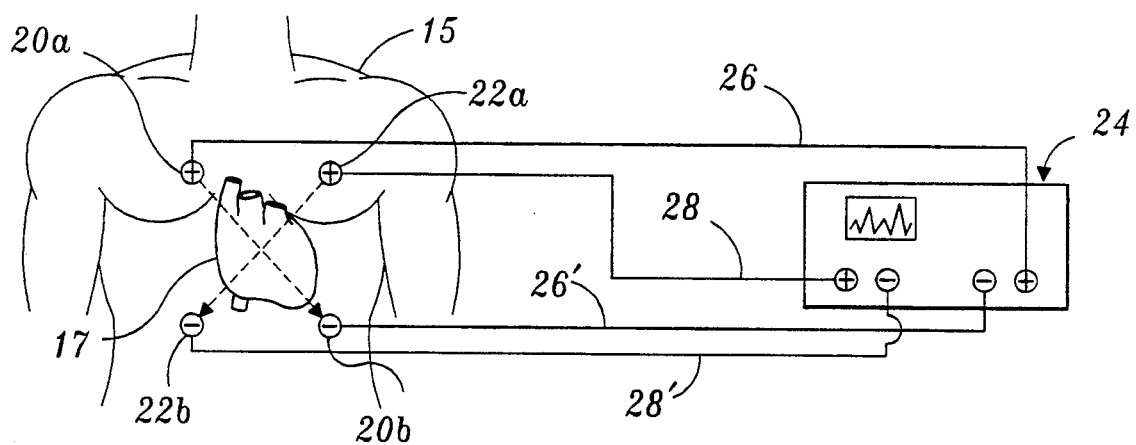
FIG. 2 is a diagram of a reduced current pacing apparatus according to a second embodiment of the present invention.

FIG. 2 is a diagram showing a second embodiment of a reduced current cardiac pacing apparatus 10 according to the present invention. Apparatus 10 comprises a plurality of electrode pairs 20 and 22, each of which further comprises a pair of positive electrodes 20a and 22a and a corresponding pair of negative electrodes 20b and 22b, respectively. Hereinafter, the term "electrode pair" is assumed to include a positive electrode and a negative electrode. During their use, electrode pairs 20 and 22 are placed on the thoracic cavity of a patient 15 such that positive electrode 20a lies in a position generally superior to the right atrium of a heart muscle 17 and negative electrode 20b is placed in a position generally inferior to the left ventricle of heart muscle 17. Similarly, positive electrode 22a is placed in a position generally superior to the left ventricle of heart muscle 17 and negative electrode 22b lies in a position generally inferior to the right ventricle of heart muscle 17. For two electrode pairs, the most effective placement of the electrodes was found to be on the front of the patient. If more than two electrode pairs are used, it may be preferable to place electrodes having one polarity on the back of the patient in a position above the heart muscle and the electrodes having the opposite polarity on the front of the patient below the heart muscle.

An electric current is provided to each of electrode pairs 20 and 22 from a current pacing apparatus 24. Current pacing apparatus 24 includes a plurality of electrically isolated current sources (not separately shown) that deliver electric pacing currents to electrode pairs 20 and 22. Because the current sources that provide the pacing currents to positive electrodes 20a and 22a are electrically isolated, all the current that enters positive electrode 20a will flow to negative electrode 20b. This is because an electric circuit must always follow a closed path. Similarly, any current that enters positive electrode 22a must flow to negative electrode 22b.

Figure 3:
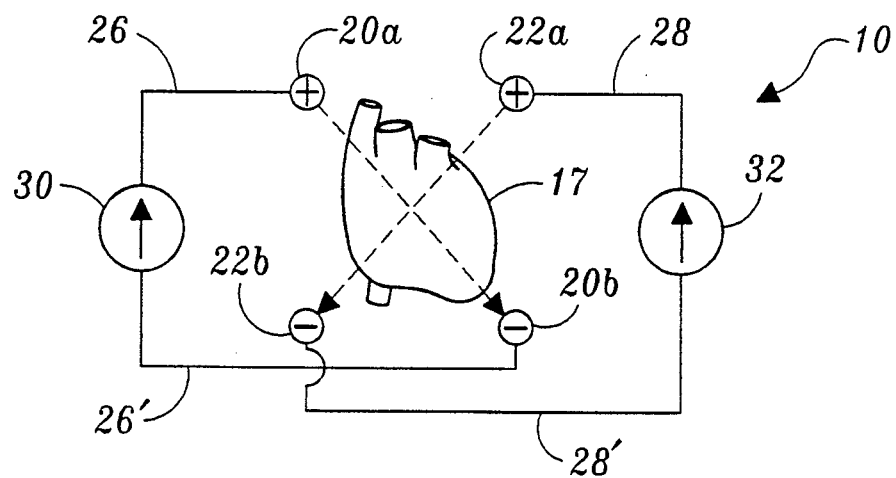
FIG. 3 is an electrical schematic diagram of the reduced current pacing apparatus according to the second embodiment of the present invention as shown in FIG. 2.

FIG. 3 shows an electrical schematic diagram of an electrically isolated current source 30 that delivers a pacing current to the pair of electrodes 20a and 20b. Isolated current source 30 delivers an individual pacing current to positive electrode 20a via a lead 26. The individual pacing current flows from positive electrode 20a over heart muscle 17 to negative electrode 20b and returns to isolated current source 30 via a lead 26'. An electrically isolated current source 32 similarly provides an individual pacing current to the pair of electrodes 22a and 22b via a lead 28 and a lead 28'. The individual pacing current flows from positive electrode 22a across heart muscle 17 to negative electrode 22b and returns to isolated current source 32 via lead 28'. The level of current provided by isolated current sources 30 and 32 is chosen to collectively cause contraction of heart muscle 17. However, the magnitude of the individual pacing currents supplied by isolated current sources 30 and 32 is chosen to avoid causing discomfort or burning to the patient.

In practice, it has been determined that, on average, 0.1 amps are required to contract a heart muscle. Therefore, in the preferred embodiment of the present invention, each electrode pair carries 0.1/n amps where n is equal to the number of electrode pairs. For example, in FIG. 2, n=2, therefore each pair of electrodes carries 0.1/2 amps. For electrode configurations having more than three electrode pairs, the total current delivered to the patient may be more than the minimum level needed to contract the heart muscle. However, the individual pacing current flowing between positive and negative electrodes that comprise an electrode pair should remain less than the level of current needed to contract the heart muscle in order to reduce patient discomfort.

The benefit of using electrically isolated current sources can be seen by comparing the isolated current sources and electrode configuration of FIG. 2 with the current source and electrode configuration shown in FIG. 1. As previously discussed, in FIG. 1, the set of pacing electrodes 5 are driven in parallel by a common pacing current source 12. Because positive electrodes 5a, 5b, and 5c and negative electrodes 5a', 5b', and 5c' are connected in parallel, more current will tend to flow between the positive electrode and negative electrode having the lowest inter-electrode impedance. If one of the impedances Ra, Rb, or Rc is relatively low, the electrode pair associated with that impedance will carry a relatively high proportion of the overall current delivered to the heart. For example, if Ra and Rb are both much greater than Rc, a large portion of the current delivered to electrode set 5 will flow between positive electrode 5c and negative electrode 5c'. As long as some current flows between electrodes 5a and 5a' and 5b and 5b', the current density at electrodes 5c and 5c' is still less than would be experienced with a single pair of electrodes. The arrangement shown in FIG. 2 is preferred, however, because the current delivered by each isolated current source is not affected by impedances other than that between the pair of electrodes to which the isolated current source is connected. Therefore, even if the impedances between the various electrode pairs differ, it is possible to control and limit the current flowing through a patient between a given pair of electrodes so that the current density is roughly one-third the density that would have been experienced if a single electrode set were used.

Figure 4:
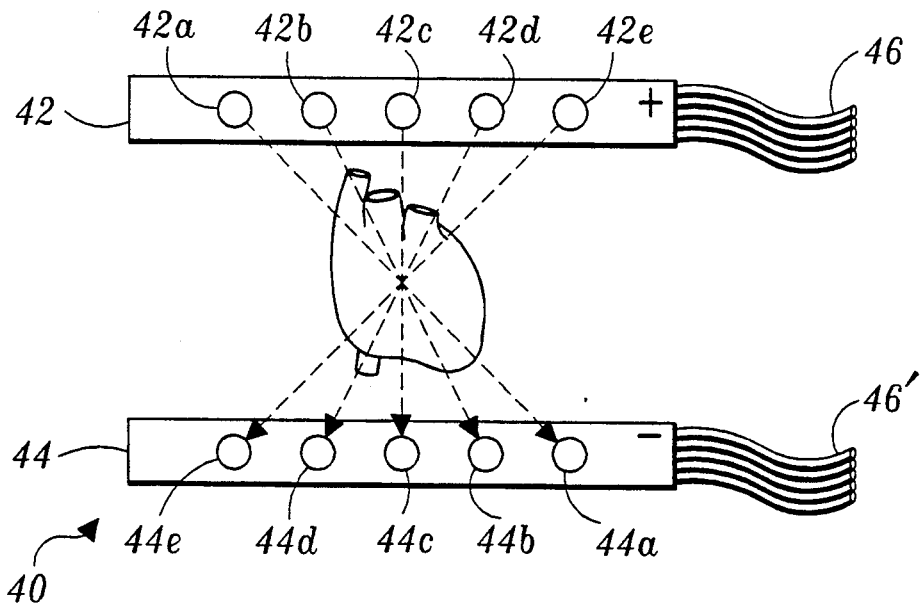
FIG. 4 is an alternative embodiment of the reduced current pacing apparatus according to the present invention.

FIG. 4 shows an alternative embodiment of a reduced current cardiac pacing apparatus, generally at reference numeral 40. Cardiac pacing apparatus 40 includes two electrode strips 42 and 44. Electrode strips 42 and 44 respectively comprise a plurality of positive electrodes 42a, 42b, 42c, 42d, and 42e and corresponding negative electrodes 44a, 44b, 44c, 44d, and 44e. A plurality of electrically isolated current sources (not shown) are connected to electrode strips 42 and 44 via leads 46 and 46'. The isolated current sources are connected such that a plurality of individual pacing currents flow diagonally across heart muscle 17. For example, an individual pacing current flows between positive electrode 42a and negative electrode 44a. Similarly, individual pacing currents flow between positive electrode 42b and negative electrode 44b, between positive electrode 42c and negative electrode 44c, etc. In this embodiment of the invention, wherein there are five electrode pairs, each electrode pair, e.g., 42b and 44b, carries an individual pacing current of smaller magnitude than the total pacing current required to contract the heart muscle. Yet, the total current delivered to all of the electrodes may be greater than the current needed to contract the heart muscle. Although the preferred embodiments have been disclosed as dividing the total required pacing current equally between electrode pairs, it is recognized that any division of the required total pacing current is possible as long as each electrode pair conveys a level of current that will reduce patient burning or discomfort.

Figure 5:
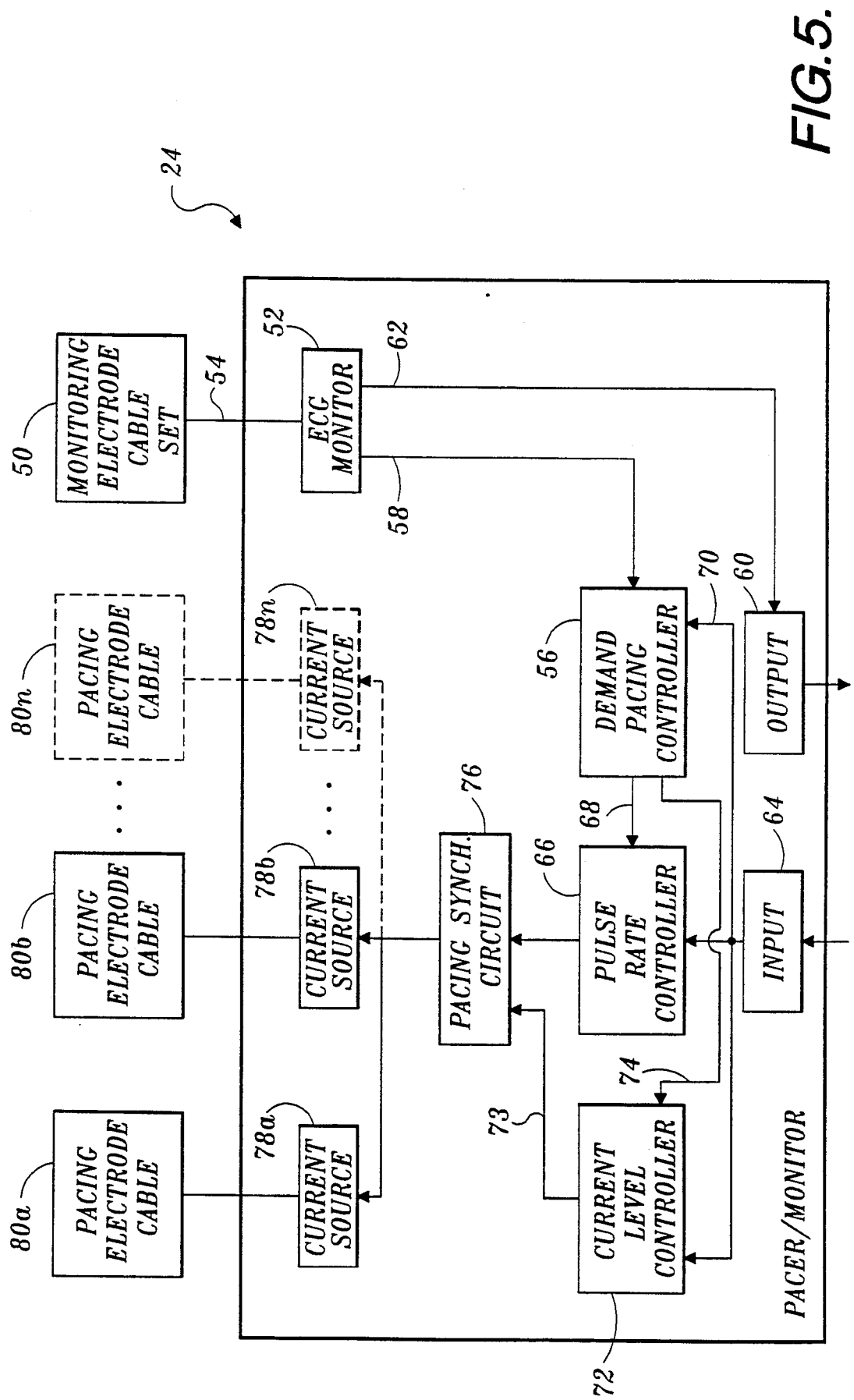
FIG. 5 is a block diagram of a cardiac pacing unit that incorporates a reduced current pacing apparatus according to the present invention.

FIG. 5 is a block diagram of a cardiac pacing apparatus 24 that incorporates the present invention. Cardiac pacing apparatus 24 may be a standalone unit or incorporated within either a multiple function pacing/defibrillator or electrocardiogram (ECG) monitoring unit. A set of monitoring cables 50 carries electrical signals from the patient to an ECG monitor 52 via a lead 54. ECG monitor 52 provides ECG signals to a demand pacing controller 56 via a lead 58 or to an output port 60 via a lead 62. An input port 64 is connected to demand pacing controller 56 by a lead 70 to enable an operator to selectively operate cardiac pacing apparatus 24 in either a demand mode or a continuous pacing mode. In a continuous pacing mode, a pacing current signal is applied to the heart at a continuous rate regardless of the ECG signal of the patient. In a demand mode, pacing current signals are applied only in the absence of spontaneous ECG signals generated by the heart muscle.

Demand pacing controller 56 is typically used to initiate the application of a pacing current signal to the heart muscle upon the occurrence or non-occurrence of a particular portion of an ECG signal (not shown). For example, if the heart is working intermittently, i.e., the patient's body is sometimes generating the proper ECG signals, but not reliably, then demand pacing controller 56 delivers appropriate pacing current signals in order to ensure that the heart operates properly. Should the natural ECG signal fail, demand pacing controller 56 provides a pacing current signal to the patient's heart at a time when the heart muscle would have received its own spontaneous ECG signal.

A pulse rate controller 66 controls the rate at which pacing current signals are delivered to the heart in response to a manual input or possibly a signal from demand pacing controller 56 transmitted over a lead 68. For example, a signal transmitted from demand pacing controller 56 to pulse rate controller 66 may instruct the pulse rate controller to increase or decrease the rate at which pacing current signals are delivered to the heart. Alternatively, input port 64 is connected to pulse rate controller 66 via lead 70 to provide means for entry of a manual setting of the rate at which pacing current signals are delivered to the heart.

A current level controller 72 controls the magnitude of the individual pacing currents delivered to each of the electrode pairs. Because patients may require different levels of pacing current to get the heart to beat properly, the magnitude of each of the individual pacing currents may need to be adjusted. Should the total pacing current delivered to the electrode pairs collectively be too small to contract the heart muscle, the level of current being delivered can be increased manually by a signal from input port 64 that is transmitted to current level controller 72 via lead 70. Alternatively, demand pacing controller 56 may be programmed to detect that the heart has not responded as desired. As a result, demand pacing controller 56 signals current level controller 72 via a lead 74 to increase the magnitude of the individual pacing currents delivered.

A pacing synchronizing circuit 76 controls the operation of a plurality of electrically isolated current sources 78a-78n. The plurality of electrically isolated current sources 78a-78n provide pacing current signals to a plurality of pacing electrode cables 80a-80n, respectively. Pacing synchronizing circuit 76 is provided to ensure that the pacing current signals delivered to electrode cables 80a-80n arrive at the heart muscle at the correct time to collectively restore the heart to normal operation.

Another use for pacing synchronizing circuit 76 is to vary the individual pacing currents that are delivered to the electrode pairs to vary the direction of the total pacing current. By altering the time at which the individual pacing currents are delivered to the electrode pairs or the magnitude of the individual pacing currents, it is possible to change the direction of the total pacing current flowing across the heart muscle. Pacing synchronizing circuit 76 can be programmed, based on clinical data, to alter the direction of the total pacing currents delivered to the electrode pairs to test a heart muscle's susceptibility to various cardiac arrythmias.

As can be seen, cardiac pacing unit 24 delivers a plurality of individual pacing currents to a patient. Each pacing current has a magnitude less than the total amount of current needed to contract a heart muscle. As the individual pacing currents flow across the heart muscle, they add to produce a total pacing current having sufficient magnitude to contract the heart muscle. Patient discomfort or burning is reduced by keeping the magnitude of the individual pacing currents low.

Although the present invention has been described with respect to its preferred embodiments, those skilled in the art will realize that changes may be made in form and scope without departing from the spirit of the invention. Therefore, the scope of the invention is should be determined solely by reference to the following claims.

The embodiments of the invention in which an exclusive property or privilege is claimed are defined as follows:

1. An external cardiac pacing apparatus for delivering a total cardiac pacing current to a patient's heart muscle comprising:
   a plurality of electrode pairs attachable to the patient's chest; and
   a plurality of isolated current sources, each of which is coupled to one pair of each of the plurality of electrode pairs, wherein each of the isolated current sources includes means for delivering an individual pacing current to one of each of the electrode pairs at substantially the same time such that the individual pacing currents delivered by the plurality of isolated current sources additively form a total cardiac pacing current, wherein each individual pacing current has a magnitude less than the total cardiac pacing current.

2. An external cardiac pacing apparatus for delivering a total cardiac pacing current to a patient's heart muscle comprising:
   a plurality of electrode pairs attachable to the patient's chest; and
   a plurality of isolated current sources, each of which is coupled to one pair of each of the plurality of electrode pairs, wherein each of the isolated current sources includes means for simultaneously delivering an individual pacing current to one of each of the electrode pairs such that the individual pacing currents delivered by the plurality of isolated current sources additively form a total cardiac pacing current, wherein each individual pacing current has a magnitude less than the total cardiac pacing current;

pulse controller means for causing the plurality of isolated current sources to simultaneously deliver the individual pacing currents to the plurality of electrode pairs; and an electrocardiographic monitor coupled to the pulse controller means for sensing heart signals produced by the patient's heart muscle and for causing the pulse controller means to cause the plurality of isolated current sources to simultaneously deliver the individual pacing currents in response to the heart signals.

3. The apparatus as in claim 2, further comprising a demand pacing controller means, coupled to the electrocardiographic monitor, for causing the total cardiac pacing current to be delivered to the patient's heart muscle if the electrocardiographic monitor fails to receive a heart signal from the patient's heart muscle within a predefined time.

4. The apparatus as in claim 3, further comprising means for operating the demand pacing controller means in a continuous mode to cause the total cardiac pacing current to be delivered to the patient's heart muscle at a regular repetition rate independent of the heart signals.

5. The apparatus as in claim 2, further comprising means for causing the plurality of isolated current sources to simultaneously deliver a series of the individual pacing currents such that a series of total cardiac pacing currents are delivered to the patient at a variable repetition rate and wherein the cardiac pacing apparatus further comprises a pulse rate controller means for controlling the repetition rate.

6. The apparatus as in claim 2, further comprising a current level controller that increases the magnitude of the individual pacing currents supplied by the isolated current sources if the magnitude of the total cardiac pacing current delivered to the patient's heart muscle is insufficient to cause contraction of the heart muscle.

7. The apparatus as in claim 2, further comprising a pacing synchronizing circuit means connected to the plurality of isolated current sources, wherein the pacing synchronizing circuit means controls a time at which the isolated current sources deliver the individual pacing currents to the plurality of electrode pairs.

8. An apparatus for providing a total cardiac pacing signal to a heart muscle of a patient, wherein the total cardiac pacing signal is applied via a plurality of separate signal paths, the apparatus comprising:

a plurality of pairs of electrodes connectable to an exterior of the patient;

a plurality of electrically isolated current sources, each of which is electrically connected to one of the pairs of electrodes, wherein each electrically isolated current source includes means for providing one pair of electrodes with an individual pacing signal that flows between the associated pair of electrodes, the individual pacing signals provided to the plurality of pairs of electrodes adding to form the total cardiac pacing signal to cause contraction of the patient's heart muscle, wherein each individual pacing signal has a magnitude that is less than the magnitude of the total cardiac pacing signal; and means for controlling a magnitude of the individual pacing signals delivered to the plurality of electrode pairs by the electrically isolated current sources such that the magnitude of the total cardiac pacing signal delivered to the patient is sufficient to contract the patient's heart muscle.

9. The apparatus as in claim 8, further comprising means for synchronizing the plurality of electrically isolated current sources to deliver the individual pacing signals to a heart muscle at the correct time to cause contraction of the heart muscle.

10. The apparatus as in claim 8, further comprising pulse controller means for causing the plurality of isolated current sources to simultaneously deliver the individual pacing signals to the plurality of electrode pairs; and an electrocardiographic monitor coupled to the pulse controller means for sensing heart signals produced by the patient's heart muscle and for causing the pulse controller means to cause the plurality of isolated current sources to simultaneously deliver the individual pacing signals in response to the heart signals.

11. The apparatus as in claim 10, further comprising a demand pacing controller means, coupled to the electrocardiogram monitor, for causing the total cardiac pacing signal to be delivered to the patient's heart muscle if the electrocardiographic monitor fails to receive a heart signal from the heart muscle within a predefined time.

12. The apparatus as in claim 11, further comprising means for operating the demand pacing controller means in a continuous mode to cause the total cardiac pacing signal to be delivered to the heart muscle at a regular repetition rate independent of the heart signals.

13. The apparatus as in claim 8, further comprising means for causing the plurality of electrically isolated current sources to deliver a series of the individual pacing signals such that a series of total cardiac pacing signals are delivered to the patient at a variable repetition rate and wherein the apparatus further comprises a pulse rate controller means for controlling the repetition rate.

14. The apparatus as in claim 8, further comprising a current level controller means that increases the magnitude of the individual pacing signals supplied by the electrically isolated current sources if the magnitude of the total cardiac pacing signal delivered to the heart muscle is insufficient to cause contraction of the heart muscle.

15. The apparatus as in claim 8, further comprising a pacing synchronizing circuit means connected to the plurality of electrically isolated current sources, wherein the pacing synchronizing circuit means controls a time at which the electrically isolated current sources deliver the individual pacing signals to the plurality of electrode pairs.

16. The apparatus as in claim 8, further comprising a pacing synchronizing circuit means for altering the individual pacing signals delivered to the plurality of electrode pairs to vary a direction of the total cardiac pacing current produced by the individual pacing signals.

17. A method of providing an external total cardiac pacing signal to a heart muscle of a patient, comprising:

producing a plurality of isolated individual pacing signals each having a magnitude that is less than a magnitude of the total cardiac pacing signal to be delivered to a plurality of electrode pairs attachable to the patient;

simultaneously delivering to the plurality of electrode pairs the plurality of isolated individual pacing signals such that the plurality of isolated individual pacing signals add to produce the total cardiac pacing signal.

18. The method of claim 17, further comprising the steps of:

monitoring the patient's heart for heart signals; and delivering the plurality of isolated individual pacing signals to the heart muscle in response to the heart signals monitored.

19. The method of claim 17, further comprising the steps of:

increasing an amplitude of the plurality of isolated individual pacing signals if the total cardiac pacing signal is insufficient to cause contraction of the heart muscle.

20. The method of claim 17, further comprising the step of:

varying a direction of the total cardiac pacing signal by altering the plurality of isolated individual pacing signals delivered to the plurality of electrode pairs.

21. A method of providing an external total cardiac pacing current to a patient's heart muscle, comprising the steps of:

producing a plurality of individual pacing currents; and delivering, at substantially the same time each of the plurality of individual pacing currents to a pair of isolated electrodes attachable to the patient, such that the plurality of individual pacing currents add to produce a total cardiac pacing current in the patient's heart muscle.

* * * * *

UNITED STATES PATENT AND TRADEMARK OFFICE
CERTIFICATE OF CORRECTION

PATENT NO. : 5,330,506  Page 1 of 2
DATED : July 19, 1994
INVENTOR(S) : C.A. Alferness et al.

It is certified that error appears in the above-indentified patent and that said Letters Patent is hereby corrected as shown below:

Title page

Item [56]      "References Cited"      Information Cited was sent by applicant on 9/13/91, received by USPTO on 9/16/91 and considered by Examiner J. Jastrzab on 7/28/92:

Add to U.S. Patent Documents:

| | | | |
|---|---|---|---|
| --3,789,854 | 2/1974 | Lee | 128/419P |
| 3,937,226 | 2/1976 | Funke | 128/419D |
| 4,088,140 | 5/1978 | Rockland et al. | 128/419PG |
| 4,094,310 | 6/1978 | McEachen et al. | 128/419Dx |
| 4,462,406 | 7/1984 | DeCote, Jr. | 128/419PG |
| 4,535,776 | 8/1985 | Strandberg et al. | 128/419PG |
| 4,549,548 | 10/1985 | Wittkampf et al. | 128/419PG |
| 4,550,370 | 10/1985 | Baker | 364/413 |
| 4,576,170 | 10/1986 | Bradley et al. | 128/419D |
| 4,694,830 | 9/1987 | Lekholm | 128/419PG-- |

UNITED STATES PATENT AND TRADEMARK OFFICE
CERTIFICATE OF CORRECTION

PATENT NO. : 5,330,506                                    Page 2 of 2
DATED      : July 19, 1994
INVENTOR(S) : C.A. Alferness et al It is certified that error appears in the above-indentified patent and that said Letters Patent is hereby corrected as shown below:

Add to "Other Publications":

Zucker et al., "Dipolar Electrode in Heart Block," JAMA, pp. 549-552, May 18, 1963.

Signed and Sealed this

Fifteenth Day of November, 1994

Attest:

BRUCE LEHMAN

Attesting Officer            Commissioner of Patents and Trademarks